United States Patent
Ulfig et al.

(10) Patent No.: US 6,791,081 B1
(45) Date of Patent: Sep. 14, 2004

(54) METHOD FOR DETERMINING PORE CHARACTERISTICS IN POROUS MATERIALS

(75) Inventors: Robert Matthew Ulfig, Middletown, WI (US); Suzette K. Pangrle, Cupertino, CA (US); Alline F. Myers, Santa Clara, CA (US); Jeremias D. Romero, Hayward, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 41 days.

(21) Appl. No.: 10/109,517

(22) Filed: Mar. 27, 2002

(51) Int. Cl.[7] .................................................. G01B 5/28

(52) U.S. Cl. ......................... 250/307; 250/306; 73/105; 438/52

(58) Field of Search .............................. 250/306, 307, 250/310, 311; 73/105; 438/52

(56) References Cited

U.S. PATENT DOCUMENTS

| | | | | |
|---|---|---|---|---|
| 5,922,299 A | * | 7/1999 | Bruinsma et al. | ............ 423/335 |
| 5,963,417 A | * | 10/1999 | Anderson et al. | ............ 361/503 |
| 6,268,405 B1 | * | 7/2001 | Yao et al. | ................... 523/113 |
| 2002/0127326 A1 | * | 9/2002 | Boukherroub et al. | ..... 427/2.11 |
| 2003/0100123 A1 | * | 5/2003 | Schanze et al. | ............. 436/106 |

OTHER PUBLICATIONS

60/329,070.*

* cited by examiner

*Primary Examiner*—Nikita Wells
*Assistant Examiner*—Christopher M. Kalivoda
(74) *Attorney, Agent, or Firm*—Mikio Ishimaru

(57) ABSTRACT

A method for measuring porosity of nanoporous materials is provided using atomic force microscopy (AFM). A surface topology map with sub-atomic resolution is created using AFM wherein the pore shape and size can be determined by measuring the pores that intersect the top or fracture surface. For porous materials requiring more accurate measurements, small scan areas with slow scan speed and fine AFM tips are used and a general estimation on distribution can be made from a sample area.

12 Claims, 1 Drawing Sheet

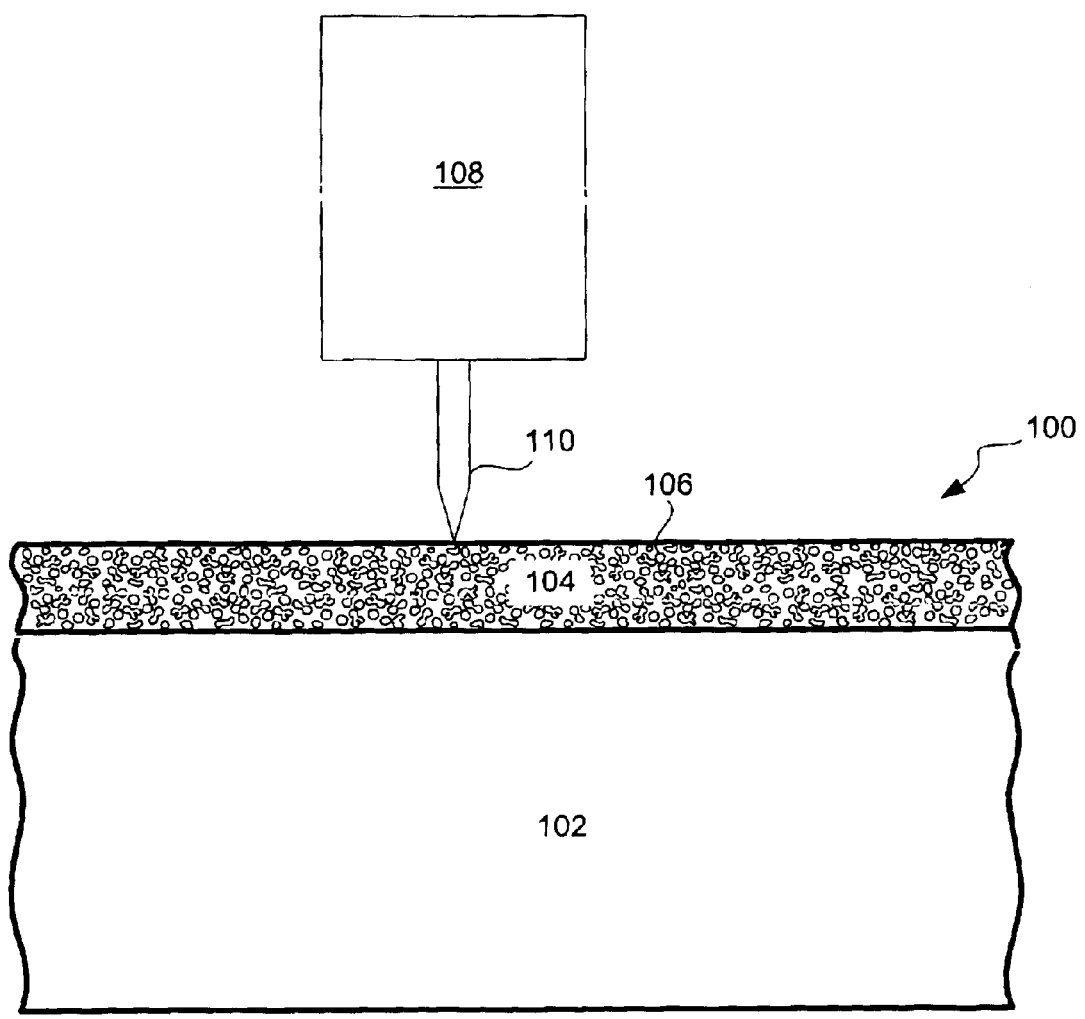

METHOD FOR DETERMINING PORE CHARACTERISTICS IN POROUS MATERIALS

TECHNICAL FIELD

The present invention relates generally to characterizing porous materials and more particularly to a method for characterizing nanoporous materials.

BACKGROUND ART

In the manufacture of integrated circuits, the dimensions of devices are scaled downwards in order to make them smaller and faster. As the dimensions further decrease, many formerly insignificant sources of error become magnified and must be monitored and compensated for. Of particular concern is the porosity of low dielectric constant (low-k) and ultra-low-k dielectric materials used as insulators in the integrated circuits.

Determining and compensating for porosity is important because it influences several significant problems. For example, to much porosity in a dielectric later can result in poor interfaces with subsequently deposed layers. Such poor interfaces can result in electromigration, movement of atoms associated with a current flow, and the formation of voids. Voids have high electrical resistance and nucleate, growing larger and eventually resulting in open circuits, which can render an integrated circuit inoperable.

Another example is in the conformal deposition of subsequent layers. In older, larger integrated circuits, the porosity of the dielectric layers did not affect the conformal deposition of subsequent layers. With the smaller devices and similarly scaled down layers that compose them and their interconnections, porosity becomes a factor, sometimes resulting in non-conformal surfaces, which can adversely affect the performance of the integrated circuit.

In addition, greater porosity makes a dielectric layer more prone to diffusion of conductor material. This is particularly common in the interconnects which connect semiconductor devices where diffusion allows conductor material to leak through the dielectric layer, eventually creating a short circuit.

Porosity, the size and interconnection of pores, can also influence the dielectric constant of the dielectric material. Because such dielectric materials are selected specifically for their dielectric constants, being able to measure the pore size and pore connectivity in the material allows for a better characterization of a material.

Also, it is extremely difficult but important to determine the shapes of the pores. Non-spherical cores have relatively sharp corners, which create electrical stress concentrations and physical stress concentrations, which lead to material failures.

Many of the above problems can be remedied or compensated for if the porosity of the dielectric material is known to a precise degree. Prior attempts to measure the porosity, pore size and pore interconnection for low-k dielectric layers have utilized scanning electron microscopy (SEM) and transmission electron microscopy (TEM) to create high-resolution images of the cross-sections. While both technologies are relatively easy to implement and are capable of creating very small images, they have proved inadequate for characterizing nanoporous materials. Nanoporous materials are materials which have microstructures with a physical order in the sub 1 E-9 meter range, such as well-known commercially available materials such as Spin On Glass (SOG), porous silicas, organic dielectric materials (such as porous SILK, a material from Dow Chemical of Midland, MI), porous LDK materials (from JSR Microelectronics, Inc., of Sunnyvale, Calif.), or organic doped silicas. The ability to simply and inexpensively characterize the pore size, interconnections, and shape for these nanoporous materials is of particular concern because currently, only methods requiring powerful and expensive equipment are adequate.

For example, Rutherford Backscattering Spectroscopy (RBS) and Positron Annihilaton Lifetime Spectroscopy (PALS) have been used in the past to measure pore size and pore connectivity, but each of these methods requires extra equipment not normally found in semiconductor fabrication plants. For example, RBS is not used in a fabrication environment because it requires an energy source to create an ion beam, which impacts the surface of the porous material. A special Rutherford Backscattering detector is then required to measure the intensity of backscattered particles. PALS works by using the variation in positron lifetimes as a function of the electron density in a material but also requires special, expensive equipment not commonly available.

Because current methods are either inadequate or inconvenient to implement, a simple method for characterizing the porosity of nanoporous materials in an inexpensive manner using commonly available equipment has been long sought but has long eluded those skilled in the art.

DISCLOSURE OF THE INVENTION

The present invention provides a method for measuring porosity of nanoporoos materials. Using atomic force microscopy (AFM), a surface topology map with subatomic resolution is created wherein the pore shape and size can be determined by measuring the pores that intersect the top or fracture surface. For porous materials requiring more accurate measurements, small scan areas with slow scan speed and fine AFM tips are used and a general estimation on distribution is made from a sample are&

The above and additional advantages of the present invention will become apparent to those skilled in the art firm a reading of the following detailed description when taken in conjunction with the accompanying drawings.

BRIEF DESCRIPTION OF THE DRAWING

The drawing is a diagram showing an Atomic Force Microscopy (AFM) tip measuring the pore size, shape, and interconnectivity in a porous material.

BEST MODE FOR CARRYING OUT THE INVENTION

Referring now to the drawing, therein is shown a system for measuring pore size and pore connectivity in a sample material 100. The sample material 100 is represented by a substrate 102 and a porous layer 104 having pores 106.

The porous layer 104 is a nanoporous material, which is a material that has microstructure pores having a physical size in the sub 1E-8 meter range and into the sub 1E-9 meter range. An Atomic Force Microscopy (AFM) tip 110 is shown measuring the pore size and pore connectivity in the sample material 100. An AFM tip 110 is shown as part of an AFM apparatus 108, which is relatively inexpensive compared to equipment used for comparable pore measurement techniques, and call be commonly found in semiconductor fabrication facilities. The AFM apparatus 108 can be opted either manually, or as part of an automated process. Using the AFM apparatus 108, the morphology, a characterization of the topology, form, and structure, of the top surface and the cross-section thickness of the porous layer 104 can be determined with subatomic, or less than or equal to 1E-8 meter, resolution. Some other pore measurement techniques are unable to provide such resolution and are therefore inadequate for measurements of this scale. Using these measurements, the pore size and shape of the porous layer 104 can be characterized.

For greater accuracy, the AFM apparatus 108 with finer AFM tips 110 can scan smaller areas of the porous layer 104 at slower speeds. Extrapolating using various mathematical techniques, an accurate estimation of pore size distribution can be made. Conversely, to map larger areas, faster scans can be made with the AFM apparatus 108.

Although the AFM technique has not previously been used for determining pore size, the use of such equipment for other reasons is common in the semiconductor industry. As a result, using AFM instead of more expensive alternatives such as RBS and PALS provides a simple, less expensive and more easily implemented alternative without sacrificing accuracy.

While the invention has been described in conjunction with a specific best mode, it is to be understood that many alternatives, modifications, and variations, will be apparent to those skilled in the art in light of the aforegoing description. Accordingly, it is intended to embrace all such alternatives, modifications, and variations that fall within the spirit and scope of the included claims. All matters hitherto-fore set forth or shown in the accompanying drawings are to be interpreted in an illustrative and non-limiting sense.

The invention claimed is:

1. A method for measuring the porosity of a porous material comprising;
   creating a morphology of the porous material using Atomic Force Microscopy, the morphology including characterization of a top surface and a cross-sectional thickness of the porous material; and
   determining the porosity using the morphology of the porous material.

2. The method as claimed in claim 1 wherein the morphology of the porous material includes a characterization of the topology, form, and structure of the top surface and the cross-sectional thickness.

3. The method as claimed in claim 1 wherein the porous material includes pores of less than about 1E-8 meter in size.

4. The method as claimed in claim 1 wherein the porous material is a material selected from a group consisting of Spin On Glass, porous silica, organic dielectric material, porous LDK material, organic doped silica, ad a combination thereof.

5. The method as claimed in claim 1 wherein the porous material is a low-k dielectric material having a dielectric constant below 3.9.

6. The method as claimed in claim 1 wherein the porous material is an ultra-low-k dielectric material having a dielectric constant below 2.8.

7. A method for measuring the porosity of a nanoporous material comprising;
   creating a morphology of the nanoporous material using Atomic Force Microscopy, the morphology including characterization of the top surface and cross-sectional thickness of the nanoporous material; and
   determining the porosity using the morphology of the nanoporous material.

8. The method as claimed in claim 7 wherein the nanoporous material includes pores of less than about 1E-9 meter in size.

9. The method as claimed in claim 7 wherein the morphology of the nanoporous material includes a characterization of the topology, form, and structure of the top surface and the cross-section thickness.

10. The method as claimed in claim 7 wherein the nanoporous material is a material selected from a group consisting of Spin On Glass, porous silica, organic dielectric material porous LDK material, organic doped silica, and a combination thereof.

11. The method as claimed in claim 7 wherein the nanoporous material is a low-k dielectric material having a dielectric constant below 3.9.

12. The method as claimed in claim 7 wherein the nanoporous material is an ultra-low-k dielectric material having a dielectric constant below 2.8.

* * * * *

UNITED STATES PATENT AND TRADEMARK OFFICE
CERTIFICATE OF CORRECTION

PATENT NO. : 6,791,081 B1
DATED : September 14, 2004
INVENTOR(S) : Ulfig et al.

It is certified that error appears in the above-identified patent and that said Letters Patent is hereby corrected as shown below:

Column 1,
Line 23, delete "to" and insert therefor -- too --; and delete "later" and insert therefor -- layer --

Column 2,
Line 3, delete "SILK" and insert therefor -- SiLK --
Line 12, delete "Annihilaton" and insert therefor -- Annihilation --
Line 19, delete "Backscattering" and insert therefor -- backscattering --
Line 34, delete "nanoporoos" and insert therefor -- nanoporous --
Line 41, delete "are&" and insert therefor -- area. --
Line 43, delete "firm" and insert therefor -- from --
Line 67, delete "call" and insert therefor -- can --

Column 3,
Line 1, delete "opted" and insert therefor -- operated --
Line 23, delete "expensive" and insert therefor -- expensive, --

Column 4,
Line 4, insert a space between the words "1" and "E-8"
Line 8, delete "ad" and insert therefor -- and --
Line 26, insert a space between the words "1" and "E-9"
Line 36, delete "material" and insert therefor -- material, --

Signed and Sealed this

Seventh Day of December, 2004

JON W. DUDAS
*Director of the United States Patent and Trademark Office*